(12) United States Patent
Yasuda et al.

(10) Patent No.: US 6,273,262 B1
(45) Date of Patent: Aug. 14, 2001

(54) PARTICLE CONCENTRATION DEVICE

(75) Inventors: Kenji Yasuda, Hiki-gun; Takeshi Sakamoto, Asaka, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/317,608

(22) Filed: May 25, 1999

(30) Foreign Application Priority Data

Jul. 14, 1998 (JP) .................................................. 10-198361

(51) Int. Cl.[7] .................................. B03B 5/66; B03B 1/00
(52) U.S. Cl. ................................. 209/1; 209/5; 209/155; 209/208
(58) Field of Search ............................... 209/1, 590, 155, 209/132, 208

(56) References Cited

U.S. PATENT DOCUMENTS

| | | | |
|---|---|---|---|
| Re. 33,524 | * 1/1991 | Schram | 209/1 |
| 4,055,491 | * 10/1977 | Parath-Furedi | 209/5 |
| 4,523,682 | * 6/1985 | Barmatz et al. | 209/1 |
| 4,743,361 | 5/1988 | Schram . | |
| 4,877,516 | * 10/1989 | Schram | 209/155 |
| 4,948,497 | * 8/1990 | Ohkawa | 209/1 |
| 5,006,266 | * 4/1991 | Schram | 209/1 |
| 5,164,094 | * 11/1992 | Stuckart | 209/155 |
| 5,225,089 | 7/1993 | Benes et al. . | |
| 5,527,460 | * 6/1996 | Trampler et al. | 209/155 |
| 5,902,489 | * 5/1999 | Yasuda et al. | 209/155 |
| 5,947,299 | * 9/1999 | Vazquez et al. | 209/1 |

FOREIGN PATENT DOCUMENTS 7-47259  2/1995  (JP) .

OTHER PUBLICATIONS

Journal of Acoustical Society of America, vol. 89, No. 5, May 1991, "Acoustical Tweezers", J. Wu, pp. 2140–2143.
Acustica, vol. 5, 1955, "Acoustic Radiation Pressure on a Compressible Sphere", K. Yosioka et al, pp. 167–178.
Journal of Acoustical Society of America, vol. 91, No. 6, Jun., 1992, "Separation devices based on forced coincidence response of fluid–filled pipes", T. Tolt et al, pp. 3152–3156.
Acustica, vol. 24, 1971, Cavitation Threshold Dependence on Volume, G. Iernetti, pp. 191–196.

* cited by examiner

*Primary Examiner*—Katherine A. Matecki
(74) *Attorney, Agent, or Firm*—Mattingly, Stanger & Malur, P.C.

(57) ABSTRACT

A device comprises a means for radiating ultrasound from one face of a chamber holding a sample solution containing particles to be concentrated, and a reflective face inclined to the face irradiated with the ultrasound. The frequency of the ultrasound radiated from the ultrasound radiating means is changed periodically and asymmetrically with the passage of time.

20 Claims, 4 Drawing Sheets

PARTICLE CONCENTRATION DEVICE

BACKGROUND OF THE INVENTION

The present invention relates to a particle concentration device, and in particular to a particle concentration device suitable for concentrating sample particles in a solution, using ultrasound.

It has been known since the 19th century that particles in a fluid can be trapped without contact by irradiating the particles with ultrasound. Concerning acoustic radiation force that particles receive when the acoustic radiation force acts on the particles, for example, in Acoust. Soc. Am. 89(1991) pp. 2140–2143, J. Wu, J. reported that he succeeded in trapping polystyrene spheres of 270 μm diameter at the focal point of focal ultrasound. As regards the principle that particles are trapped by acoustic radiation force, in Acoustica 5 (1955) pp. 167–178, K. Yosioka and Y. Kawasima reported that they calculated the intensity, in an ideal fluid, of acoustic radiation force which particles receive in a standing wave and a traveling wave, and the acoustic radiation force which the particles levitated in the standing wave receive is in proportion to the volume of the particles and the frequency of the ultrasound forming the standing wave. Furthermore, Japanese Patent laid open No. 7-47259, proposed by the present inventors, discloses a manner of introducing ultrasound into a tube in which a fluid is allowed to flow so as to focus particles continuously within some area, or a method for collecting the focused particles.

It has been known heretofore that as the frequency of ultrasound used in a standing wave is gradually changed, the position of nodes of the standing wave changes accordingly and further particles also move accordingly. In J. Acoust. Soc. Am. 91(1992), pp. 3152–3156, T. L. Tolt et al., reported a means for moving and concentrating particles trapped in nodes of a standing wave actually by sweeping, upwards and downwards, the frequency of ultrasound introduced into a fluid wherein the particles are dispersed. Furthermore, U.S. Pat. No. 5,225,089 by E. Benes et al. discloses a means for concentrating particles by raising the frequency of ultrasound radiated from an ultrasound source arranged in a channel.

Moreover, it has also been known heretofore that the position of nodes of a generated standing wave can be controlled by controlling the phases of ultrasounds radiated from a pair of opposite ultrasound vibrators for generating a standing wave. U.S. Pat. No. 4,743,361 by C. J. Schram discloses a means of applying this technique actually to measure physical properties of particles by observing how much the particles follow the movement of the position of nodes of a standing wave. It has also been reported that when ultrasound having slightly different frequencies are radiated oppositely, the position of nodes of a generated standing wave advances by the slight difference between the frequencies.

Additionally, it has been known that the generation of cavitation which may damage a sample can be suppressed by raising the frequency of used ultrasound. It has also been known that when, for example, ultrasounds having the same density are introduced, the sound pressure peak $p_c$ of its cavitation threshold is in proportion to the frequency f of the incident ultrasounds. As reported in, for example, Acustica 24 (1971) pp. 191–196 by G. Iernetti, cavitation can be prevented only by raising the frequency of ultrasound. Actually, in the step of washing silicon wafers by irradiation with ultrasound in pure water in the process of producing semiconductors, the frequency of used ultrasound is within the MHz range in order to prevent the surfaces of the silicon wafers from being damaged by cavitation based on the ultrasound.

SUMMARY OF THE INVENTION

The above-mentioned conventional techniques are techniques of introducing ultrasound into a solution containing sample particles to be concentrated so as to generate a standing wave in the solution and concentrating the particles around pressure node or pressure loops of the standing wave generated in the solution. They have a problem that, in order to concentrate the particles in the solution between the adjacent pressure nodes or pressure loops of the generated standing wave, the wavelength of the ultrasound must be strictly adjusted so that the value $(n+½)\lambda$ becomes equal to the width of the inner wall of a chamber.

Besides, in the above-mentioned conventional techniques, to make concentration efficiency maximum in a chamber having a limited volume, the frequency of incident ultrasound is adjusted so that the value $\lambda/2$ becomes equal to the width of the chamber. In this case, only one pressure node of a standing wave is generated at the center of the tube-like chamber so that particles in the chamber are concentrated around this pressure node. In this way, the concentration efficiency becomes maximum. However, the distribution of the particles has some width around the node. Thus, in the case that the concentration of the particles is high, even if the distribution of the particles reaches an equilibrium state, the particles cannot be sufficiently concentrated or separated.

Moreover, in the above-mentioned conventional techniques, when the width of the channel is made large, it is necessary to lower the frequency of the used ultrasound to make the channel width equal to the value ($\lambda/2$). However, as the frequency is lowered, the cavitation originating from the ultrasound is liable to be generated. Thus, a means for suppressing the cavitation, such as a degass module, is necessary.

An object of the present invention is to provide a particle concentration method and a particle concentration device wherein it is unnecessary to adjust the frequency of used ultrasound strictly in accordance with changes in the width of a chamber and the sort of a solvent.

Another object of the present invention is to provide a particle concentration device which can exceed the limitation of the concentration efficiency based on any conventional distribution of the particles at the time of the equilibrium state of a standing wave.

The present invention is implemented by comprising a means for radiating ultrasound from one face of a chamber holding a sample solution containing particles to be concentrated, and a reflective face inclined to the face irradiated with the ultrasound, and further causing the frequency of the ultrasound to be changed periodically and asymmetrically with the passage of time.

DESCRIPTION OF THE PREFERRED EMBODIMENT

Figure 1:
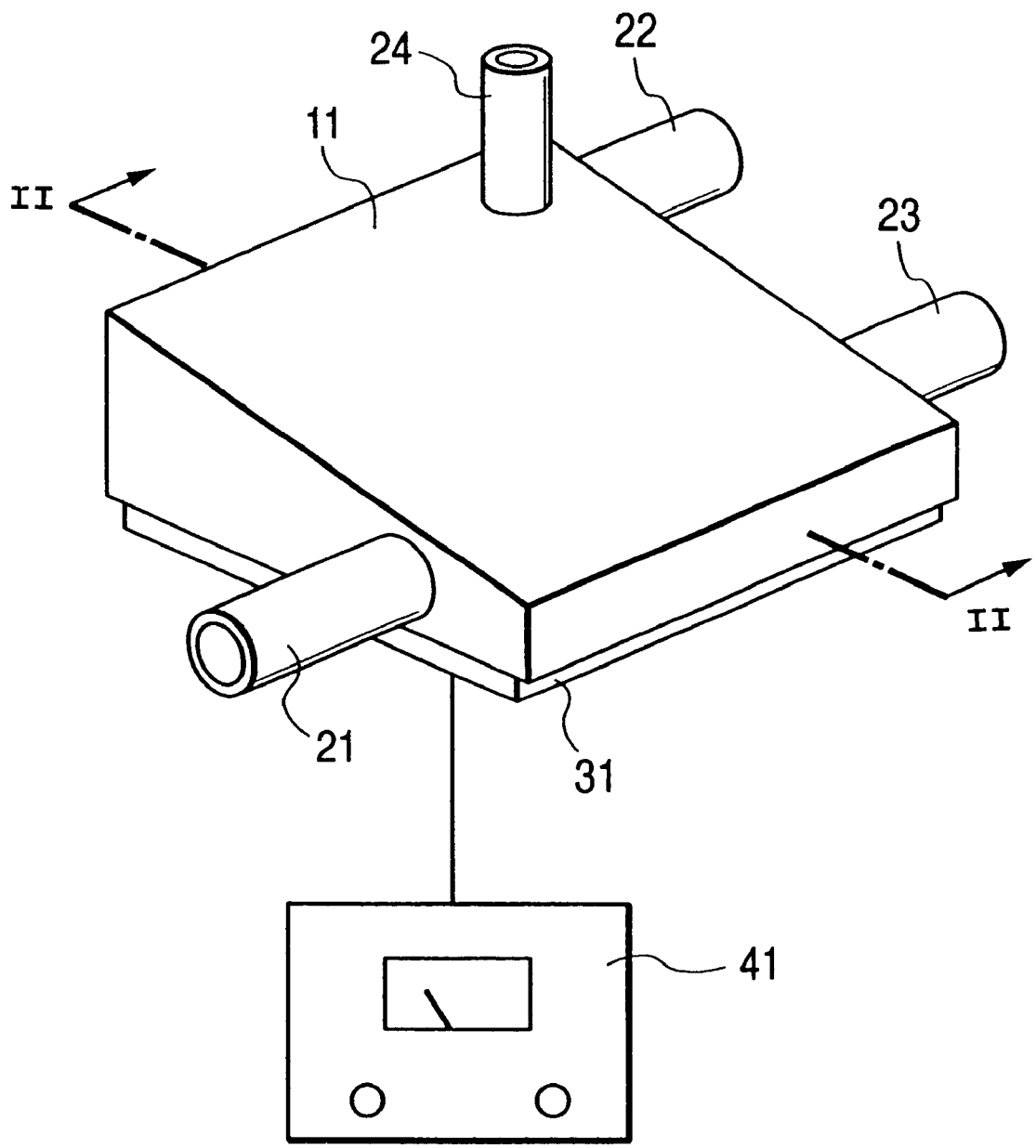
FIG. 1 is a schematic view of a first embodiment of the present invention.

A first embodiment of the particle concentration device of the present invention will be described, referring to FIG. 1, which is a schematic view of the device, and FIG. 2, which is a cross section taken on the II—II line of the device. The device of the present embodiment comprises a chamber 11 which can hold a sample solution containing particles, a tube 21 for introducing the sample solution containing the particles into the chamber 11, a tube 22 for collecting sample solution components which do not contain the particles separated by the device, a tube 23 for collecting sample solution components wherein the particles are concentrated, an air removing tube 24 for removing air bubbles remaining the chamber, an ultrasound source 31 for introducing ultrasound into the chamber 11, and a driving circuit 41 for the ultrasound source, which has a means for changing, periodically as time passes, the frequency or the intensity of the ultrasound generated by the ultrasound source 31. When ultrasound is generated, the ultrasound is introduced into the chamber 11, as shown by an arrow 51 in FIG. 2 to generate a standing wave between two nonparallel planar walls 12 and 13 in the chamber.

Figure 3:
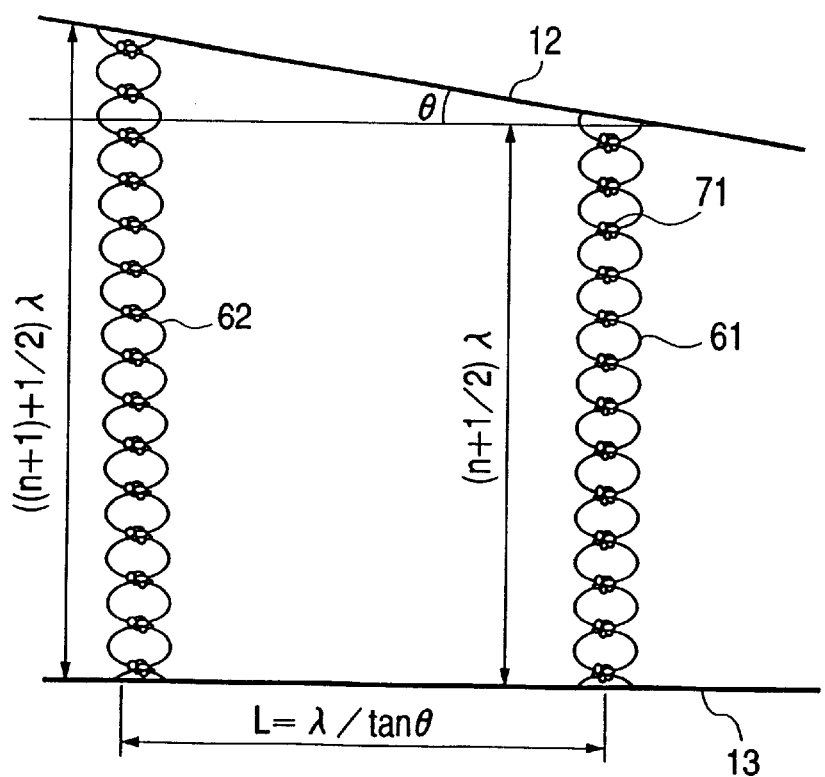
FIG. 3 is a schematic view illustrating a situation wherein standing waves are generated by ultrasound irradiated from an ultrasound source in the first embodiment of the present invention.

The standing wave generated at this time will be described referring to FIG. 3. The requirement for generating a standing wave between nonparallel planar plates opposite to each other at an angle of θ is the fact that the distance between the two planar plates becomes as follows:

$$(n+\tfrac{1}{2})\lambda \qquad \text{(formula 1)}.$$

In this equation, λ is the wavelength of the ultrasound in a sample solution, and n is an integer. It is meant that the standing wave has (2n+1) acoustic pressure nodes. Therefore, in the case that 2 walls of the chamber are inclined to each other at an angle of θ, adjacent standing waves 61 and 62 having a spatial period L are generated at constant intervals.

$$L = \lambda/\tan\theta \qquad \text{(equation 2)}$$

Particles 71 in the sample solution are trapped at the areas of acoustic pressure nodes or loops of the generated standing waves. The value of angle θ is desirable to be than less than 10° for keeping reflection of ultrasound.

In the case that a standing wave is generated between conventional parallel planar plates to concentrate particles, unless for the purpose of meeting the requirement of the equation (1) the frequency of the ultrasound generated by an ultrasonic vibrator is finely adjusted at all times to correspond to a subtle change in wavelength λ, following a change in the acoustic speed in a sample solution, the standing wave cannot be generated. In the particle concentration device of the present invention, however, a pair of the opposite walls in the chamber have a given angle θ. Thus, even if fine adjustment of its frequency as in the conventional parallel planar plates is not performed, a standing wave itself spontaneously moves at the site meeting the requirement of the equation (1) to generate a new standing wave. Therefore, it is possible to cope with a change in wavelength λ in the solution, originating from a drastic change in the composition of the solution components, and the non-uniformity of the wavelength λ in the solution, caused by non-uniform distribution of the sample solution components in the chamber, without any fine adjustment of the frequency.

Figure 4:
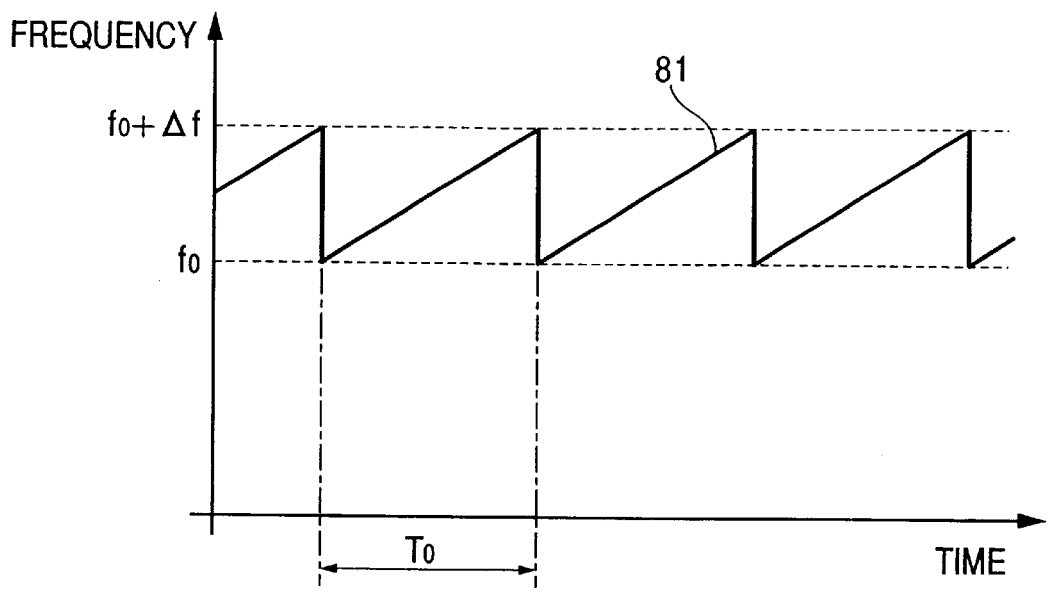
FIG. 4 is a view illustrating a change in the frequency of the ultrasound radiated in the first embodiment of the present invention as time passes.
Figure 5:
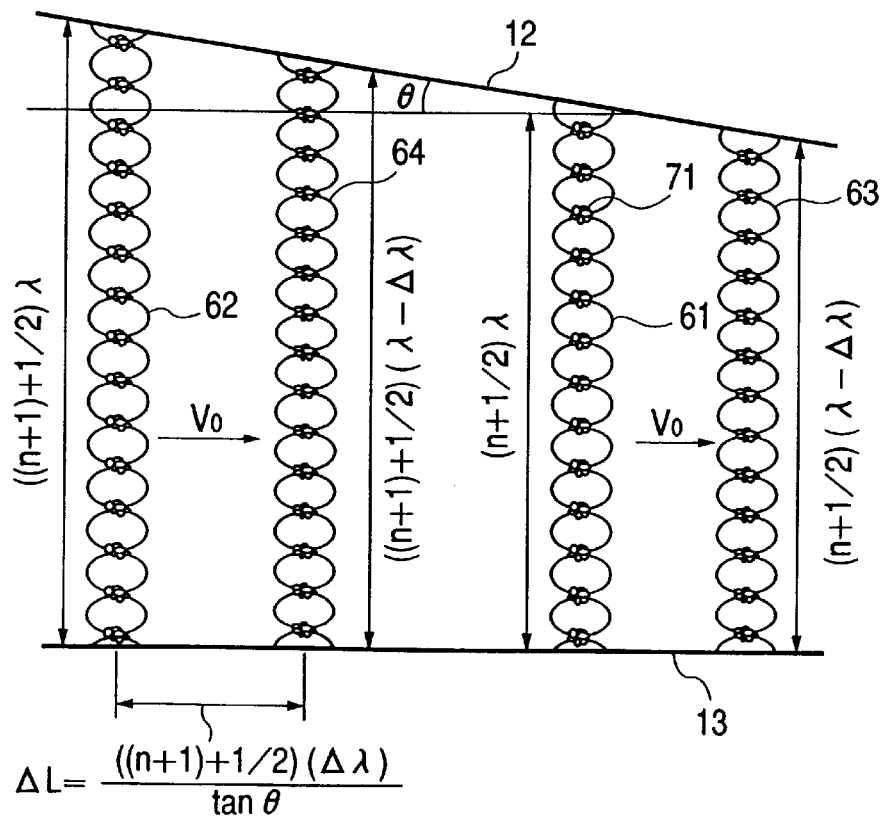
FIG. 5 is a schematic view illustrating a situation wherein the standing waves illustrated in FIG. 4 move with the passage of time by the change of the frequency of the ultrasound illustrated in FIG. 5 with the passage of time.

Next, the frequency of the ultrasonic standing wave generated in the chamber 11 is changed according to a sawtooth waveform relationship 81 between time and the ultrasonic frequency as shown in a graph of FIG. 4. In this case, it is assumed that when the frequency $f_0$ of the ultrasound rises by Δf, the wavelength λ of a standing wave is shortened by Δλ. Under this situation, as shown in FIG. 5, a standing wave 62 moves to the site of a standing wave 64 by ΔL:

$$\Delta L = \frac{((n+1)+1/2)(\Delta\lambda)}{\tan\theta} \qquad \text{(equation 3)}$$

At this time, the moving speed $V_0$ of the standing wave is as follows:

$$V_0 = \frac{\Delta L}{T_0} \qquad \text{(equation 4)}$$

wherein $T_0$ is a cycle time at which the frequency of the ultrasound is asymmetrically changed with the passage of time.

In order to attain the concentration of the particles by the change in the frequency of the ultrasound as shown in FIG. 4, the moving amount ΔL [that is, the amount generated by the fact that the particles which are present at the pressure node of the standing wave 62 when the frequency is $f_0$ move to the site of the standing wave 64 when the frequency is ($f_0$+Δf)] needs to be larger than the distance L between the adjacent standing waves 61 and 62 when the frequency is $f_0$. That is, when the requirement of the equation (5):

$$\Delta L > L, \qquad \text{(equation 5)}$$

or the equation (6):

$$(n_0+\tfrac{1}{2})(\Delta\lambda) > \lambda, \qquad \text{(equation 6)}$$

the particles are being concentrated toward the wedge-tip of the wedge-shaped chamber. In these equations, $n_0$ is an integer. In the wedge tip portion whose height is less than ($n_0+\tfrac{1}{2}$) λ in the wedge-shaped chamber 11, any concentration is not caused. Therefore, near the tip of the wedge the height of the chamber needs to be ($n_0+\tfrac{1}{2}$)λ or higher. From the sample collecting tube 23, sample solution components containing the concentrated particles can be taken out. In the same way, from the sample collecting tube 22, sample solution components which do not contain the particles can be taken out.

In FIG. 4, the frequency of the ultrasound gradually rises from $f_0$ to ($f_0$+Δf) and the particles are caused to move at a speed of $V_0$ so that the particles follow the rise in the frequency. Thereafter, the frequency is instantaneously returned to $f_0$ so that the particles do not follow this change.

Such processes are repeated to concentrate the particles. Conversely, however, the solution components containing the particles and those which do not contain the particles can be taken out from the tubes 22 and 23, respectively, by repeating the process that the frequency is gradually decreased from $(f_0+\Delta f)$ to $f_0$ and then is instantaneously returned to $(f_0+\Delta f)$. Concentration may be performed by making times for the rise and drop in the frequency simply asymmetric.

In order to suppress cavitation based on ultrasound in the present invention, it is desired to use ultrasound having a frequency of 500 kHz or higher.

EMBODIMENT II

Figure 2:
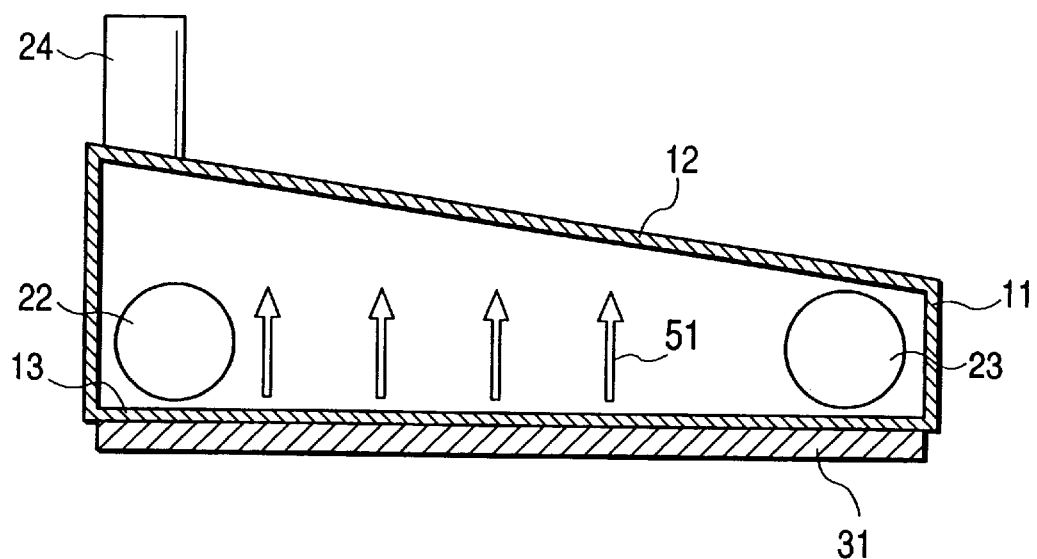
FIG. 2 is a cross section taken on 2—2 line II—II of the first embodiment shown in FIG. 1, which is viewed in the direction of arrows.
Figure 6:
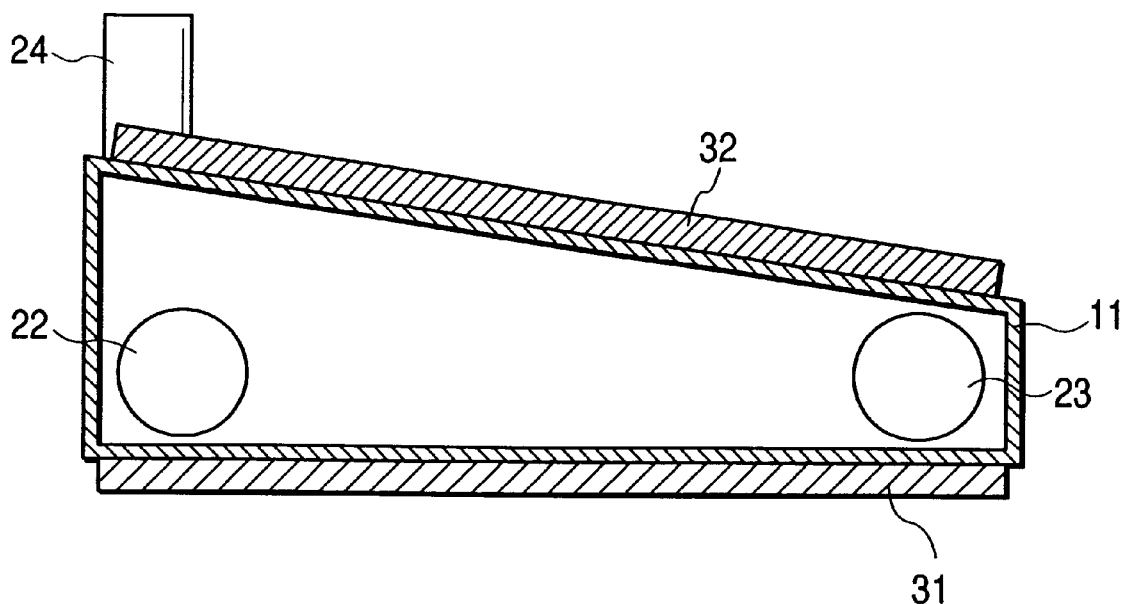
FIG. 6 is a cross section II—II of a second embodiment of the present invention, which is viewed in the direction of arrows.

In the first embodiment shown in FIG. 1, the ultrasound source 31 is arranged at only one side of the wedged-shaped chamber. As shown in FIG. 6, however, in a similar way an ultrasound source 32 may be arranged on the upper face of the chamber to improve the generation efficiency of standing waves. The second embodiment shown in FIG. 6 is the same as in the first embodiment except that the ultrasonic source 32 is arranged on the upper face of the chamber.

EMBODIMENT III

Figure 7:
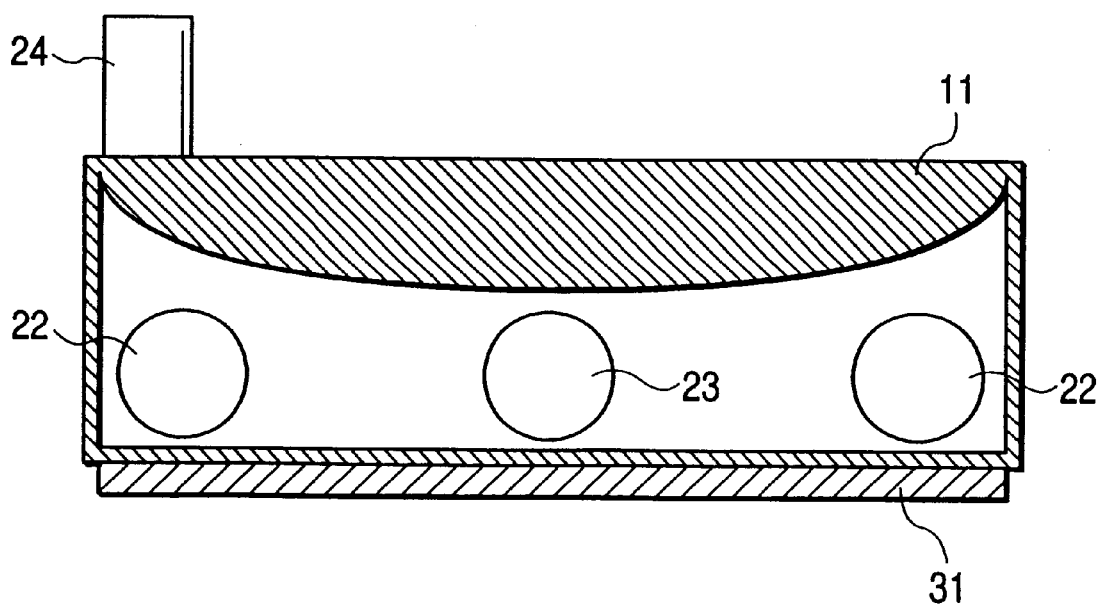
FIG. 7 is a cross section of a third embodiment, corresponding to the section taken on II—II of the first embodiment, which is viewed in the direction of arrows.

In a third embodiment shown in FIG. 7, the central area of a chamber is an area having the smallest height. Particles introduced from right and left sample-introducing tubes 22 get together at the center of the chamber, so that the particles are collected at the center of the chamber.

As described above in detail, the present invention has an advantage that particles in a fluid can be continuously concentrated and separated without contact.

What is claimed is:

1. A particle concentration device, comprising a chamber having a first face and a reflective second face, means for radiating ultrasound from said first face of said chamber holding a sample solution containing particles to be concentrated, said reflective face inclined to said first face and being irradiated with the ultrasound, means for changing periodically the frequency of the ultrasound radiated from the ultrasound radiating means with the passage of time, means for introducing a sample solution into the chamber, means for collecting concentrated sample particle components from the chamber, and means for collecting sample solution components which do not contain the particles from the chamber.

2. The particle concentration device according to claim 1, wherein the frequency of the ultrasound radiating means is at least 500 kHz.

3. The particle concentration device according to claim 1, wherein the angle of the reflective face against the first face is less than 10 degrees.

4. A particle concentration device comprising:

a chamber having a first face and a reflective second face, ultrasound radiating means for radiating ultrasound from said first face of said chamber holding a sample solution containing particles, said reflective face being inclined to the first face, and an ultrasound controlling means for changing the frequency of the ultrasound periodically so that the particles come together to a given site of the chamber.

5. The particle concentration device according to claim 4, wherein the ultrasound controlling means changes the frequency of the ultrasound periodically and asymmetrically with the passage of time.

6. The particle concentration device according to claim 5, further comprising, means for introducing the sample solution into the chamber, means for collecting concentrated sample particle components from the chamber, and means for collecting sample solution components which do not contain the particles from the chamber.

7. The particle concentration device according to claim 6, wherein the frequency of the ultrasound is at least 500 kHz.

8. A particle concentration device comprising:

a wedge-shaped chamber having an inlet into which a sample solution containing particles to be concentrated is introduced, a first outlet near a wedge tip of the wedge-shaped chamber, a second outlet at a portion opposite to the wedge tip, and two planar walls inclined to each other at a preset angle;

an ultrasound source which is disposed on at least one of the two planar walls and radiates an ultrasound into the wedge-shaped chamber; and a driving circuit for generating the ultrasound by the ultrasound source such that the frequency of the ultrasound irradiated from the ultrasound source changes periodically, by repeating a first process and a second process, wherein, in said first process, the frequency of the ultrasound is gradually increased from $f_0$ to $f_0+\Delta f$ as time passes such that the particles follow the increase of the frequency of the ultrasound and the particles trapped at areas of acoustic pressure nodes or loops of an ultrasonic standing wave generated between the two planar walls are caused to move toward the wedge tip at a moving speed of the ultrasonic standing wave, and wherein, in said second process, the frequency of the ultrasound is instantaneously decreased from $f_0+\Delta f$ to $f_0$ such that the particles do not follow the decrease of the frequency of the ultrasound, for concentrating the particles in the sample solution near the wedge tip in the wedge-shaped chamber.

9. The particle concentration device according to claim 8, wherein a relation $\Delta L > L$ is satisfied, wherein L is a distance between two adjacent ultrasonic standing waves generated between the two planar walls when the frequency of the ultrasound is $f_0$, and $\Delta L$ is a distance between the ultrasonic standing wave generated between the two planar walls when the frequency of the ultrasound is $f_0$ and the ultrasonic standing wave generated between the two planar walls when the frequency of the ultrasound is $f_0+\Delta f$.

10. The particle concentration device according to claim 8, wherein a solution containing the concentrated particles is collected from the wedge-shaped chamber near the wedge tip through the first outlet.

11. The particle concentration device according to claim 8, wherein a solution not containing the particles is collected from the wedge-shaped chamber at the portion opposite to the wedge tip through the second outlet.

12. The particle concentration device according to claim 8, wherein the preset angle is less than 10 degrees.

13. A particle concentration device comprising:

a wedge-shaped chamber having an inlet into which a sample solution containing particles to be concentrated is introduced, a first outlet near a wedge tip of the wedge-shaped chambers, a second outlet at a portion opposite to the wedge tip, and two planar walls inclined to each other at a preset angle;

an ultrasound source which is disposed on at least one of the two planar walls and radiates an ultrasound into the wedge-shaped chamber; and a driving circuit for generating the ultrasound by the ultrasound source such that the frequency of the ultrasound irradiated from the ultrasound source changes periodically, by repeating a first process and a second process, wherein, in said first process, the frequency of the ultrasound is gradually decreased from $f_0+\Delta f$ to $f_0$ as time passes such that the particles follow the decrease of the frequency of the ultrasound and the particles trapped at areas of acoustic pressure nodes or loops of an ultrasonic standing wave generated between the two planar walls are caused to move toward the portion opposite to the wedge tip at a moving speed of the ultrasonic standing wave, and wherein, in said second process, the frequency of the ultrasound is instantaneously increased from $f_0$ to $f_0+\Delta f$ such that the particles do not follow the increase of the frequency of the ultrasound, for concentrating the particles in the sample solution at the portion opposite to the wedge tip in the wedge-shaped chamber.

14. The particle concentration device according to claim 13, wherein a relation $\Delta L > L$ is satisfied, wherein L is a distance between two adjacent ultrasonic standing waves generated between the two planar walls when the frequency of the ultrasound is $f_0$, and $\Delta L$ is a distance between the ultrasonic standing wave generated between the two planar walls when the frequency of the ultrasound is $f_0$ and the ultrasonic standing wave generated between the two planar walls when the frequency of the ultrasound is $f_0+\Delta f$.

15. The particle concentration device according to claim 13, wherein a solution not containing the particles is collected from the wedge-shaped chamber near the wedge tip through the first outlet.

16. The particle concentration device according to claim 13, wherein a solution containing the concentrated particles is collected from the wedge-shaped chamber at the portion opposite to the wedge tip through the second outlet.

17. The particle concentration device according to claim 13, wherein the preset angle is less than 10 degrees.

18. A particle concentration device comprising:

a wedge-shaped chamber having an inlet into which a sample solution containing particles to be concentrated is introduced, two outlets, and two planar walls inclined to each other at a preset angle;

an ultrasound source which is disposed on at least one of the two planar walls and radiates an ultrasound into the wedge-shaped chamber; and a driving circuit for generating the ultrasound by the ultrasound source such that the frequency of the ultrasound irradiated from the ultrasound source changes periodically, by repeating a first process and a second process, wherein, in said first process, the frequency of the ultrasound is gradually changed from a first frequency to a second frequency such that the particles follow the change of the frequency of the ultrasound and the particles trapped at areas of acoustic pressure nodes or loops of an ultrasonic standing wave generated between the two planar walls are caused to move toward a wedge tip of the wedge-shaped chamber or a portion opposite to the wedge tip at a moving speed of the ultrasonic standing wave, and wherein, in said second process, the second frequency of the ultrasound is instantaneously changed for the first frequency of the ultrasound is such that the particles do not follow the change of the frequency of the ultrasound, for concentrating the particles in the sample solution near the wedge tip or the portion opposite to the wedge tip in the wedge-shaped be chamber.

19. The particle concentration device according to claim 18, wherein a solution containing concentrated particle s and a solution not containing the particles are collected separately from the wedge-shaped chamber through the two outlets, respectively.

20. A particle concentration device comprising:

a wedge-shaped chamber having first and second planar walls which are inclined to each other at a preset angle, and a sample solution containing particles to be concentrated being introduced into the wedge-shaped chamber;

an ultrasound source which is disposed on the first wall and radiates an ultrasound toward the second wall as a reflective face in the wedge-shaped chamber; and a driving circuit for generating the ultrasound by the ultrasound source such that the frequency of the ultrasound irradiated from the ultrasound source changes periodically, by repeating a first process and a second process, wherein, in said first process, the frequency of the ultrasound is gradually changed from a first frequency to a second frequency such that the particles follow the change of the frequency of the ultrasound and the particles trapped at areas of acoustic pressure nodes or loops of an ultrasonic standing wave generated between the first and second walls are caused to move toward a wedge tip of the wedge-shaped chamber or a portion opposite to the wedge tip at a moving speed of the ultrasonic standing wave, and wherein, in said second process, the second frequency of the ultrasound is instantaneously changed for the first frequency such that the particles do not follow the change of the frequency of the ultrasound, for concentrating the particles in the sample solution near the wedge tip or the portion opposite to the wedge tip in the wedge-shaped chamber.

* * * * *